United States Patent [19]
Eggensperger et al.

[11] Patent Number: 5,276,047
[45] Date of Patent: Jan. 4, 1994

[54] LIQUID 1,2-BENZOISOTHIAZOLINE-3-ONE PREPARATION

[75] Inventors: Heinz Eggensperger; Peter Oltmanns; Karl-Heinz Scheler, all of Hamburg; Karl-Heinz Diehl, Norderstedt, all of Fed. Rep. of Germany

[73] Assignee: Sterling Winthrop, Inc., New York, N.Y.

[21] Appl. No.: 10,050

[22] Filed: Jan. 28, 1993

Related U.S. Application Data

[63] Continuation-in-part of Ser. No. 779,560, Oct. 18, 1991, abandoned.

[51] Int. Cl.⁵ .................... A61K 31/425; A61K 31/33
[52] U.S. Cl. ..................................... 514/373; 514/674
[58] Field of Search ................... 514/372, 373, 674

[56] References Cited

U.S. PATENT DOCUMENTS

| | | | |
|---|---|---|---|
| 4,379,137 | 4/1983 | Ehlers et al. | 514/372 |
| 4,683,233 | 7/1987 | Salzburg et al. | 514/373 |
| 4,923,887 | 5/1990 | Bauer et al. | 514/373 |

FOREIGN PATENT DOCUMENTS

| | | |
|---|---|---|
| 1191253 | 5/1970 | United Kingdom . |
| 1320531 | 6/1973 | United Kingdom . |
| 1330531 | 9/1973 | United Kingdom . |

Primary Examiner—Joseph Paul Brust
Assistant Examiner—Mary Susan H. Gabilan
Attorney, Agent, or Firm—John R. Everett

[57] ABSTRACT

The invention relates to a liquid preparation containing 1,2-benzoisothiazoline-3-one (BIT) and amines and optionally containing additional solvents and common additives, and containing as amine one or more amines having the general formula

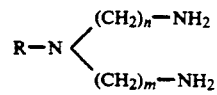

wherein R represents a straight-chained or branched alkyl or alkylene radical having 10 to 14 C atoms; $n+m$ has a value of 4 to 12 and neither n nor m can be zero. The liquid composition, in an amount of at least 0.05 to 0.3% (by weight), can be used in products which contain water or can be diluted with water such as dispersions of synthetic materials, emulsion paints, adhesives, paper-coating materials, textile softening agents, sizing agents, surfactants, detergents, cleaning and polishing agents, spinning baths, coolants or metal working fluids, leather auxiliaries, and silicone and bitumen emulsions, as agent against material destruction caused by microbes.

8 Claims, No Drawings

LIQUID 1,2-BENZOISOTHIAZOLINE-3-ONE PREPARATION

This application is a continuation-in-part of U.S. Ser. No. 07/79,560 filed Oct. 18, 1991, now abandoned.

FIELD OF THE INVENTION

The invention relates to a liquid preparation of 1,2-benzoisothiazoline-3-one (BIT) with an amine.

BACKGROUND OF THE INVENTION

The 1,2-benzoisothiazoline-3-one (BIT) has been known as anti-microbially active substance and is used as preservative in technical applications or, in general, as an additive which is suitable to counteract material destruction ("Mikromatz", in german) caused by microbes. To make this compound available in a convenient preparation that can be metered easily, an aqueous dispersion may be prepared with the crude BIT obtained during synthesis. Such dispersions, however, are not stable when stored and will settle in the course of time. GB Patent 11 91 253 has disclosed aqueous solutions of crude BIT with two or more amine compounds of the series comprising the diethanol amine, triethanol amine, diisopropanol amine, triisopropanol amine or morpholine; these aqueous solutions contain BIT in the form of a mixture of the amine salts. Furthermore, GB Patent 13 30 531 has disclosed that BIT amine salts can be imparted with better stability in a cold environment when they are present in the form of solutions in aliphatic, cycloaliphatic or heterocyclic amines having 2 to 6 C atoms and do not have hydroxyl and ether groups. The effectiveness of these preparations against material destruction, however, frequently is not adequate.

SUMMARY OF THE INVENTION

The present invention provides a liquid preparation of 1,2-benzoisothiazoline-3-one (BIT) and amines, and optionally with a content of additional solvents and common additives, characterized in that it contains, as an amine, one or more amines having the general formula

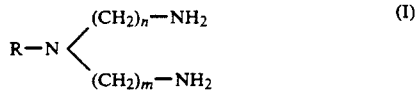

(I)

wherein R represents a straight-chained or branched alkyl or alkylene radical having 10 to 14 C atoms; n+m has a value of 4 to 12 and neither n nor m can be zero.

The invention provides new liquid preparations of BIT and amines which are stable on storage and exhibit a surprising synergistic effect against microbial destruction in technical applications, particularly in technical products, which contain water or can be diluted with water. They can be made into stable products with only water as solvent, and therefore are more suitable from the viewpoints of ecology, as well as human toxicology.

DETAILED DESCRIPTION OF THE INVENTION

The preparations of the invention herein may consist on one hand only of BIT and one or more amines having Formula I and not contain additional solvents. In this case, the BIT content is restricted to a maximum of 10% by weight to improve keeping and handling properties.

On the other hand, preparations with a higher BIT concentration and amines in accordance with Formula I may be provided with one or more additional solvents.

Solvents which can be used, other than water are solvents which can be mixed with water such as low-molecular univalent, divalent and trivalent alcohols, glycols, di- and polyglycols, ether of glycols, di- and polyglycols such as ethanol, isopropanol, propanediol-1,3,glycerin, butanetriol-1,2,3,butanetriol-1,2,4,ethylene glycol, diethylene glycol, triethylene glycol, polyethylene glycol, dipropylene glycol, ethylene glycol monomethylether, ethylene glycol monoethylether, ethylene glycol monopropylether, ethylene glycol monobutylether, diethylene glycol monomethylether, diethyl glycol monoethylether, diethylene glycol monopropylether, diethylene glycol monobutylether, diethylene glycol dimethylether and diethylene glycol diethylether, whereby the use of dipropylene glycol and butyl diglycol are preferred.

Liquid preparations containing BIT and organic amines in accordance with Formula I and optionally other solvents should have a molecular ratio of BIT relative to the amines of at the most 3:1. With this concentration ratio, the entire BIT is converted into its amine salt. In the case of an amine having Formula I, where R=lauryl and both m and n=3, this means a ratio of 10 parts by weight of BIT to 6.6 parts by weight of amine. This weight ratio is attained in accordance with representative preparations 1 through 5 and 9 of Table 1.

Useful organic amines having Formula I include those wherein R is $C_{10}$- through $C_{14}$-, straight-chained or branched alkyl or alkenyl amines.

Particularly preferred are preparations where the amine compounds having Formula I have as substituent R a lauryl radical and both n and m have a value of 3. Such amines are used preferably in an amount of 3 to 30%, together with approximately 5 to 35% by weight of BIT, in addition to the solvent, wherein the solvent consists essentially of glycols and advantageously even of water, including dilute (0.5% by weight) sodium hydroxide solutions. For example, such a composition may consist of 5 to 30% by weight of BIT, 3 to 20% by weight of an amine having Formula I, 25 to 40% by weight of a glycol-containing solvent and 67 to 10% by weight of water.

In another embodiment, a preparation of the invention, in particular when producing low-emission preparations, may contain more or less organic solvents, whereby, in order to obtain preparations which are stable in a cold environment and when stored, the amine compound should be used in at least twice the amount necessary for BIT salt formation. For example, such a composition would then contain 5 to 20% by weight of BIT and 6.5 to 26% by weight of the organic amine compound having Formula I and 88.5 to 54% by weight of water.

Other conventional additives may be nonionic, cationic and/or anionic surfactants used as emulsifying or dispersing agents or as solubilizers, whereby the amount of said additives is up to 25%, and preferably, 5 to 25% and, in particular 10 to 20%.

Additional additives may be known complexing agents and/or water-softening agents which are suitable for complexing calcium, magnesium or iron ions. The contents of these additives usually is below approximately 15% by weight and, preferably, not above 10% by weight, with respect to the preparation. Furthermore, conventional additives may be color-imparting additives, aromatic substances, flavors, turbidity-providing substances and, of course, other disinfecting components.

The liquid preparation of the invention herein is suitable for use in industrial products which contain water or can be mixed with water and are used against destruction by microbes, in particular in liquid systems such as, for example, in the case of dispersions of synthetic materials using polystyrene, polyacrylate or polyvinyl acetate and further in emulsion paints, adhesives, paper-coating materials, textile-softening agents and sizing agents, in detergents, cleaning and polishing agents, spinning baths, coolants or metal working fluids, leather-auxiliaries and in silicone and bitumen emulsions.

The inventive preparation is preferably used in a concentration of 0.05 to 0.3% by weight, with respect to the substrate to be preserved.

Apart from the principal inventive liquid preparation which, in the simplest case, consists of 10% by weight of BIT and 90% by weight of the amine compound and represents a high viscous clear solution which may be combined with additional additives, the following Preparations of Table 1 provide more detailed information, whereby the concentration data relate to the content of active ingredients. In order to prepare the liquid preparations of the invention, it is useful if the amine compound is first mixed with the solvents and any optionally required auxiliary substances, followed by the addition of BIT and stirring at temperatures of 40° to 50° C. until a clear solution is attained.

TABLE 1

|  | Weight % |
|---|---|
| Preparation 1 | |
| 1,2-benzoisothiazoline-3-one | 35 |
| lauryldipropylenetriamine | 23 |
| dipropylene glycol | 22 |
| butyl diglycol | 20 |
| Preparation 2 | |
| 1,2-benzoisothiazoline-3-one | 10 |
| lauryldipropylenetriamine | 6.6 |
| dipropylene glycol | 83.4 |
| Preparation 3 | |
| 1,2-benzoisothiazoline-3-one | 30 |
| lauryldipropylenetriamine | 20 |
| dipropylene glycol | 38 |
| water | 12 |
| Preparation 4 | |
| 1,2-benzoisothiazoline-3-one | 5 |
| lauryldipropylenetriamine | 3.3 |
| butyl diglycol | 50 |
| 1,2-propylene glycol | 25 |
| water | 16.7 |
| Preparation 5 | |
| 1,2-benzoisothiazoline-3-one | 10 |
| lauryldipropylenetriamine | 6.6 |
| dipropylene glycol | 50 |
| water | 33.4 |
| Preparation 6 | |
| 1,2-benzoisothiazoline-3-one | 10 |
| lauryldipropylenetriamine | 13.2 |
| water | 76.8 |
| Preparation 7 | |
| 1,2-benzoisothiazoline-3-one | 18 |
| lauryldipropylenetriamine | 35 |
| water | 47 |
| Preparation 8 | |
| 1,2-benzoisothiazoline-3-one | 20 |
| lauryldipropylenetriamine | 26 |

TABLE 1-continued

|  | Weight % |
|---|---|
| water | 54 |
| Preparation 9 | |
| 1,2-benzoisothiazoline-3-one | 10 |
| lauryldipropylenetriamine | 6.6 |
| water | 63.4 |
| ethoxylated fatty alcohol with 11 EO | 20 |
| Preparation 10 | 10 |
| 1,2-benzoisothiazoline-3-one | 18 |
| lauryldipropylentriamine | 8 |
| dihydroxyethylglycin sodium salt | 0.5 |
| sodium hydroxide | to 100 |
| water | |

The synergistic effectiveness increase achieved with the inventive preparations is obvious from the results of a serial dilution test which was performed with a preparation of the invention and compared with the effectiveness individual substances of that same preparation.

The test was carried out in accordance with the guidelines of the Deutsche Gesellschaft für Hygiene und Mikrobiologie (German Association for Hygiene and Microbiology). The steps of dilution ranged from 5000, 2500, 1250 to 9.8 μg/mL. The tested germs were: Staphylococcus aureus (Staph. aureus) Pseudomonas aeruginosa (Ps. aeruginoso) Candida albicans (C. albicans) Penicillium funiculosum (P. funiculosum) Aspegillus niger (A. Niger)

The minimum inhibiting concentrations (MIC values) of Example A representing an inventive preparation, Examples B and C containing only the component benzoisothiazoline-3-one, and Example D containing only the component lauryldipropylenetriamine were determined.

Inventive Example A was contained 10% of benzoisothiazoline-3-one, 10% of lauryldipropylenetriamine, 30% of dipropylene glycol and 50% of water.

Reference Example B in accordance with DE Patent 28 40 273 contained 10% of benzoisothiazoline-3-one, 5.9% of sodium hydroxide solution (45%), 30% of dipropylene glycol and 54.1% of water.

Reference Example C in accordance with GB Patent 11 92 253 contained 10% of benzoisothiazoline-3-one, 6.7% of ethylene diamine, 30% of dipropylene glycol and 53.3% of water.

Reference Example D contained 10% of lauryldipropylenetriamine, 30% of dipropylene glycol and 60% of water.

In order to demonstrate the synergism, the synergism index, (SI) was calculated in accordance with F. C. Kull, P. C. Eisman, H. D. Slverstrowicz and R. L. Mayer, Applied Microbiology 9 (1961)538, according to the following formula:

$$\frac{Q_A}{Q_a} + \frac{Q_B}{Q_b} = SI$$

wherein $Q_a$ and $Q_b$, respectively, represent the amount of components A and B alone, respectively; and $Q_A$ and $Q_B$, respectively, represent the amount of the respective component in a mixture of A and B which is required to arrive at a defined end point.

If SI<1, a synergism exists: in the case of a SI=1 a strictly additive effect is achieved; and a SI>1 represents an antagonism.

At the end point of this serial dilution test that concentration must be set which just barely still inhibits the growth of the micro-organisms, i.e., minimum inhibiting concentration (MIC).

Therefore, in order to calculate the SI values, the MIC values of the tested examples can be related to each other.

$$SI = \frac{MIC \text{ Example A}}{MIC \text{ Examples B or C}} + \frac{MIC \text{ Example A}}{MIC \text{ Example D}}$$

The SI values listed in the table below illustrate the presence of a synergism. It is particularly distinct in the case of the germs *Ps. aeruginosa* and *A. niger* which are particularly relevant in practical applications. The result compared with known BIT formulations offers a more balanced spectrum of efficacy with lower concentrations of active components.

|  | Example MIC Values μg/ml] | | | | |
| --- | --- | --- | --- | --- | --- |
| Germ | A | B | C | D | SI |
| Staph. aureus | 78 | 312 | 312 | 625 | 0.38 |
| Ps. aeruginosa | 312 | 2500 | 2500 | 2500 | 0.25 |
| C. albicans | 156 | 312 | 312 | 5000 | 0.53 |
| P. funiculosum | 78 | 156 | 156 | 5000 | 0.52 |
| A. niger | 312 | 1250 | 1250 | 5000 | 0.31 |

The invention has been described in detail with particular reference to certain preferred embodiments thereof, but it will be understood that variations and modifications can be effected within the spirit and scope of the invention.

What is claimed is:

1. Liquid composition of 1,2-benzoisothiazoline-3-one (BIT) and amines characterized in that it contains one or more amines having the general formula

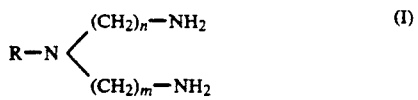

wherein R represents a straight-chained or branched alkyl or alkylene radical having 10 to 14 C atoms; n+m has a value of 4 to 12 and neither n nor m can be zero.

2. Liquid composition in accordance with claim 1 characterized in that it contains an amine having the general Formula I, wherein n+m has a value of 6.

3. Liquid composition in accordance with claim 1 or 2, characterized in that it consists of 10% by weight of BIT and at least 90% by weight of amines having Formula I.

4. Liquid composition in accordance with claim 1 or 2, characterized in that it contains BIT and amines having Formula I in a molecular ratio of at the most 3:1.

5. Liquid composition in accordance with claim 1 characterized in that it contains 10% by weight of BIT and 18% by weight of lauryldipropylentriamine.

6. Liquid composition in accordance with claim 1 or 2, characterized in that it contains 5 to 35% by weight of BIT, up to 95% by weight of amines having Formula I, and a diluent of the group comprising glycol ether, glycols and water.

7. Liquid composition in accordance with claim 1 or 2, characterized in that it contains 0–20% by weight of a complexing agent.

8. A liquid composition comprising water and a compositions according to any one of the preceding claims.

* * * * *